United States Patent [19]
Kliger

[11] 3,935,863
[45] Feb. 3, 1976

[54] SURGICAL SPONGE

[76] Inventor: Herbert L. Kliger, 29 Harvard St., P.O. Box 541, Brookline Village, Mass. 02147

[22] Filed: July 19, 1974

[21] Appl. No.: 489,991

[52] U.S. Cl. ................................ 128/296; 128/269
[51] Int. Cl.² B32B 31/20; A61F 13/00; A61B 10/00
[58] Field of Search .......... 128/2 B, 2 W, 269, 270, 128/296

[56] References Cited
UNITED STATES PATENTS

| | | | |
|---|---|---|---|
| 3,097,636 | 7/1963 | Haynes, Jr. et al. | 128/2 W |
| 3,324,855 | 6/1967 | Heimlich | 128/296 X |
| 3,394,702 | 7/1968 | Heimlich et al. | 128/269 |
| 3,481,335 | 12/1969 | Beutlich | 128/270 |
| 3,731,682 | 5/1973 | Fielding | 128/269 |
| 3,837,950 | 9/1974 | Reimels | 128/296 |

Primary Examiner—Aldrich F. Medbery
Attorney, Agent, or Firm—Robert E. Ross

[57] ABSTRACT

A pre-formed surgical sponge to be used with or without suction in surgical procedures. The sponge has generally a cup or pouch shape and is formed of porous or sponge-like material such as non-woven cloth, polyurethane foam or other plastic foams. In one embodiment of the invention the sponge is readily detachable from the tip, so that it can be rapidly replaced during a surgical operation.

4 Claims, 5 Drawing Figures

SURGICAL SPONGE

BACKGROUND OF THE INVENTION

In surgical operations, it is often necessary to remove fluid such as blood and other body fluids from the body cavity being operated on. This is commonly done with a tube connected to a suction device. However, since the fluid may contain solid particles, and since trauma would reslt if living tissue is drawn into the suction tube, it is customary to lay down a sponge in the body cavity and press the end of the suction tube against the sponge, so that any fluid is drawn into the suction tube through the sponge without picking up tissue, preventing clogging of the suction tube and preventing contact beteem living tissue and the end of the suction tube, a two-fold function. Such a procedure is time consuming and inconvenient, and there is the ever present danger of a sponge being left in the body cavity.

DESCRIPTION OF THE ILLUSTRATED EMBODIMENT

Figure 1:
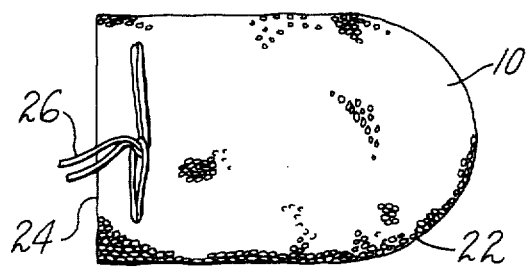
FIG. 1 is view in side elevation of a shield for a surgical suction rube embodying the features of the invention.

Referring to the drawing, there is illustrated a surgical sponge 10 for assembly onto a surgical suction tube 12, to prevent body tissue from being sucked into the tube during use, and to filter out solid particles in the fluid that might clog the suction tube.

In the illustrated embodiment the suction tube 12 has a rear end portion 14 adapted to be attached to a suction supply hose 15 and an elongated forward portion terminating in an open end 16. An enlarged portion 18 is provided to facilitate grasping by the fingers during use.

The tube 12 is a standard surgical appliance in common use, and as described hereinbefore it has been customary to use the tube 12 in conjunction with a surgical sponge of common shape by pressing the end of the tube against the sponge.

However, in accordance with this invention, the surgical sponge 10 is pre-formed to provide a cavity to receive the end of the suction tube. In the illustrated embodiment the shield 10 is generally pouch-shaped, formed of two pieces of porous, inert material such as polyurethane foam which are adhesively secured or heat sealed together at the periphery 22, except at the rear end 24. To removably retain the shield on the tube, cords 26 are secured to the shield near the rear end thereof in such a manner that the cord passes through both halves of the shield.

Figure 2:
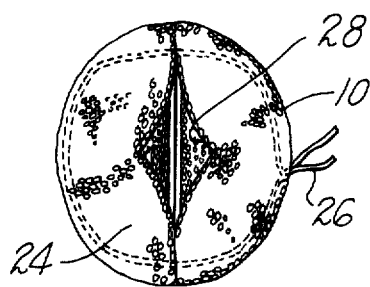
FIG. 2 is a view of FIG. 1 as seen from the left end.
Figure 3:
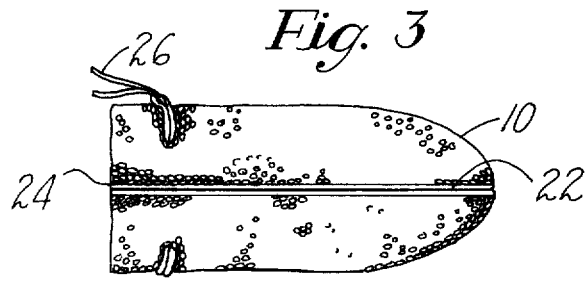
FIG. 3 is a view of FIG. 1 as seen from the bottom.
Figure 4:
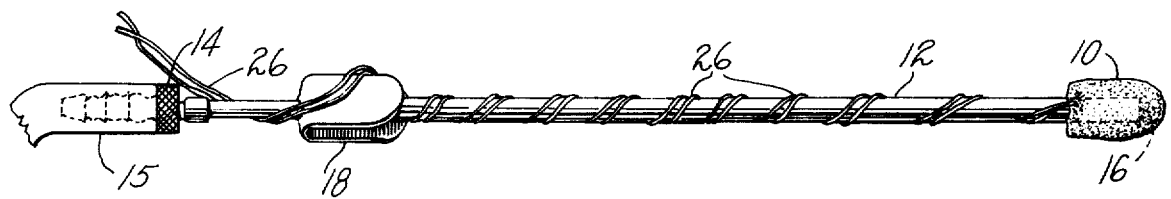
FIG. 4 is a view in side elevation of a suction tube with the shield and FIG. 1 assembled therein.
Figure 5:
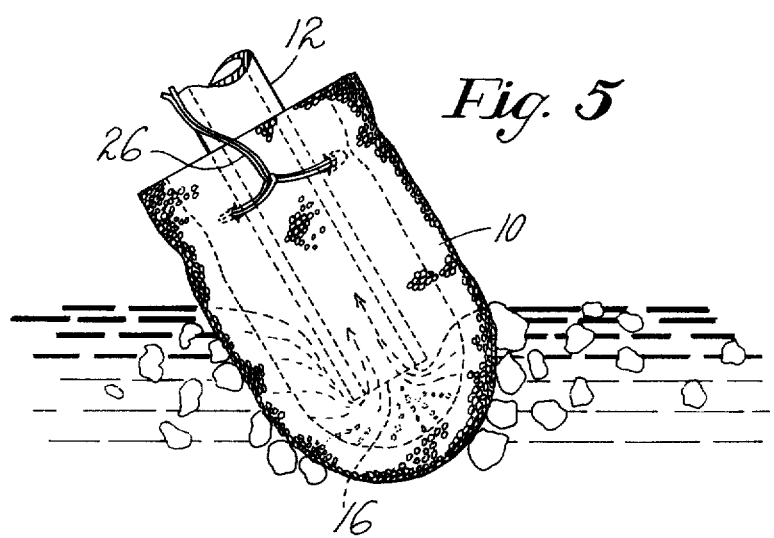
FIG.5 is a view of the forward end of the suction tube of FIG. 1 operating to remove fluid from a body cavity.

The shield (sponge) can be easily and rapidly assembled onto the tube by pressing the opposite edges together, so that the two portions at the rear of the sponge spread apart, forming an opening 28 (see FIG. 2). The tube may then be inserted into the sponge cavity and the cords pulled tight and spirally wrapped around the tube. The cords have sufficient length that when so wrapped it extends beyond the enlarged portion 18. The cords may be tightly fastened to the tube but it is not necessary as it will be held in fixed relation to the tube by the fingers during use. A removal force will be applied to the sponge 10 during use only when the tube is withdrawn from the body cavity, and the pressure of the fingers against the string will prevent the sponge 10 from being pulled off of the tube during such removal.

After removal the sponge 10 may be easily removed by pulling it off of the end of the tube, and a fresh sponge assembled.

During use, the presence of the porous sponge retained on the end of the tube allows the tube to be pressed against body tissue in the body cavity without stopping the flow of fluid into the tube and without causing trauma to delicate tissue in the body cavity. The sponge also serves to filter out any particles in the fluid that might clog the suction tube, such as blood clots, yet allows smaller particles normally present in the blood to pass through.

Although in the illustrated embodiment the sponge is in the form of a pouch formed of two pieces secured together, for convenience in manufacturing from available materials without expensive tools, it will be understood that the sponge may also be made of a single piece of material formed into a cup shape, dimensioned to fit closely over the end of the suction tube.

The sponge may be made of any one of a number of materials, such as foams of various materials such as polyurethane, laminates of cloth and foams, or woven or non-woven filter cloth. It may also be impregnated or combined with an X-ray detectable material.

Since certain other obvious changes may be made in the specific embodiment of the invention illustrated, it is intended that all matter contained herein be interpreted in an illustrative and not in a limiting sense.

I claim:

1. A surgical sponge for use in a body cavity comprising a porous sponge material pre-formed to provide a cup-shaped member having an internal opening and having a mouth to the internal opening dimensioned to freely receive the end of a suction tube, means for releasably securing the sponge to the end of said suction tube comprising an attaching cord having an adjustable tightening means on one end secured to the sponge adjacent the mouth thereof for attaching and securing said sponge to the suction tube said cord having a length such that the other end remote from the sponge can be disposed above a portion of the suction tube and sponge that remains outside the body cavity.

2. A surgical sponge according to claim 1 in which the sponge is impregnated with an X-ray detectable material.

3. A surgical sponge according to claim 1 in which the cup-shaped member is formed of two similar flat sheet portions joined together at their edges.

4. A surgical sponge for use in a body cavity comprising a porous sponge material preformed to provide a cup-shaped member having an internal opening and having a mouth to the internal opening dimensioned for loosely fitting the end of a suction tube, means for releasably securing the sponge to the end of the said suction tube comprising an attaching cord having an adjustable tightening means on one end secure to the sponge adjacent the mouth thereof for attaching and securing said sponge to the suction tube, said cord having a length such that the other end remote from the sponge can be disposed above a portion of the suction tube and sponge that remains outside the body cavity.

* * * * *